United States Patent [19]
Chiappetta

[11] Patent Number: 5,989,229
[45] Date of Patent: Nov. 23, 1999

[54] NEEDLE COVER ASSEMBLY HAVING SELF-CONTAINED DRUG APPLICATOR

[75] Inventor: Paul Chiappetta, Basking Ridge, N.J.

[73] Assignee: Becton, Dickinson and Company, Franklin Lakes, N.J.

[21] Appl. No.: 08/864,609

[22] Filed: May 28, 1997

[51] Int. Cl.$^6$ .................................................. A61M 5/00
[52] U.S. Cl. ............................ 604/263; 604/1; 604/164; 604/192; 604/289; 604/310
[58] Field of Search .................. 604/1, 2, 3, 162, 604/171, 199, 192, 198, 263, 264, 265, 266, 267, 280, 283, 164, 158, 523, 533, 289, 310, 311

[56] References Cited

U.S. PATENT DOCUMENTS

| | | |
|---|---|---|
| 1,687,472 | 10/1928 | Dorman et al. . |
| 1,711,352 | 4/1929 | Jeffreys ........................................ 604/1 |
| 3,270,743 | 9/1966 | Gingras . |
| 3,587,575 | 6/1971 | Lichtenstein ............................ 604/199 |
| 3,977,401 | 8/1976 | Pike . |
| 4,243,035 | 1/1981 | Barrett . |
| 4,362,157 | 12/1982 | Keeth . |
| 4,392,859 | 7/1983 | Dent ........................................ 604/198 |
| 4,482,348 | 11/1984 | Dent ........................................ 604/198 |
| 4,557,720 | 12/1985 | Hemphill ..................................... 604/1 |
| 4,636,201 | 1/1987 | Ambrose et al. ........................ 604/192 |
| 4,747,719 | 5/1988 | Parkin .......................................... 604/3 |
| 4,781,693 | 11/1988 | Martinez et al. ........................ 604/175 |
| 4,799,926 | 1/1989 | Haber ....................................... 604/199 |
| 4,811,847 | 3/1989 | Reif et al. . |
| 4,950,252 | 8/1990 | Luther et al. . |
| 4,952,204 | 8/1990 | Korteweg .................................... 604/1 |
| 4,988,341 | 1/1991 | Columbus et al. ...................... 604/306 |
| 5,000,193 | 3/1991 | Heelis et al. ................................ 604/1 |
| 5,015,228 | 5/1991 | Columbus et al. ........................ 604/51 |
| 5,059,186 | 10/1991 | Yamamoto et al. .................... 604/280 |
| 5,242,425 | 9/1993 | White et al. ............................. 604/256 |
| 5,312,371 | 5/1994 | Dombrowski et al. ................. 604/198 |
| 5,342,320 | 8/1994 | Cameron ................................. 604/198 |
| 5,417,668 | 5/1995 | Setzer et al. ............................ 604/263 |
| 5,489,267 | 2/1996 | Moreno et al. ........................... 604/89 |
| 5,531,810 | 7/1996 | Fullemann . |
| 5,562,633 | 10/1996 | Wozencroft ............................. 604/171 |

FOREIGN PATENT DOCUMENTS 096314   12/1983   European Pat. Off. .

Primary Examiner—Ronald K. Stright, Jr.
Attorney, Agent, or Firm—Eric M. Lee

[57] ABSTRACT

A needle cover assembly is provided that incorporates a drug applicator therein. The needle cover assembly includes an inner sleeve and an outer sleeve. The inner sleeve is formed from a hard material and acts as a needle shield. The inner sleeve also includes an absorbent material thereon that can absorb a drug such as an antimicrobial agent. This allows the absorbent material to be swabbed on the patient's skin prior to puncturing with a needle. The outer sleeve covers the absorbent material and prevents evaporation of the drug from the absorbent material.

2 Claims, 4 Drawing Sheets

NEEDLE COVER ASSEMBLY HAVING SELF-CONTAINED DRUG APPLICATOR

BACKGROUND OF THE INVENTION

This invention relates to the field of medical devices. More particular this invention relates to a needle cover assembly that is used in conjunction with a medical device employing a needle or trocar for puncturing the skin or outer wall of a body cavity.

Many medical procedures are invasive, requiring the clinician to insert a medical device through the patient's skin or into the body cavity. Such invasive procedures are needed to infuse fluid into a patient, to withdraw fluid from a patient, or to manipulate tissue inside the patient. For example, hypodermic syringes inject medication into a patient through a needle; an intravascular catheter uses an introducer needle to place the catheter into the patient's vasculature; and a trocar is used to puncture a hole in the patient's body wall to provide a path for placement of laparoscopic surgical equipment, angiography, angioplasty or arthrectomy catheters.

Before a needle or trocar can be employed, the patient's skin where the needle or trocar is to be placed must be disinfected. Otherwise, bacteria on the patient's skin will be able to enter the patient's body and infect the patient. Typically, a cotton swab, either held directly by the clinician or indirectly via an integral handle or a separate handle such as by the use of forceps, is soaked with an antimicrobial agent. Such antimicrobial agents include alcohol, povidone iodine or chlorhexidine. The cotton swab is rubbed over the patient's skin to thoroughly wet the skin with the antimicrobial agent and thus disinfect the patient's skin. After the patient's skin is disinfected, the cotton swab is discarded and the skin is punctured with the needle or the trocar.

Although this procedure is generally satisfactory, it could be improved. For example, the medical device and the antimicrobial agent are typically supplied separately. Indeed, in many instances the antimicrobial agent is also supplied separately from the cotton swab or applicator. This results in separate inventory management for the healthcare entity which can be expensive. In addition, in emergency situations, the clinician may waste valuable time in locating the proper antimicrobial agent and applicator before the medical procedure can begin. In addition, many traditional applicators require the clinician to directly contact the antimicrobial agent during application to the patient. Finally, in many developing countries, the proper disinfecting protocol may not be followed because of the shortcomings described above.

SUMMARY OF THE INVENTION

It is therefore an object of this invention to provide a needle cover assembly that minimizes the number of separate items needed to prepare the patient's skin and cover the needle or trocar of a medical device.

It is also an object of this invention to allow a clinician to disinfect a patient's skin without the need for the clinician to directly contact the antimicrobial agent.

This invention combines a needle cover and a drug applicator into one assembly. This assembly includes an inner sleeve and an outer sleeve.

The inner sleeve fits over the needle and is removably connected to the needle hub or some other fixed portion of the medical device to cover the needle and prevent premature exposure of the needle. The inner sleeve also includes an applicator portion. This applicator portion is preferably located along a distal portion of the inner sleeve and is formed by adhering an absorbent material to the inner sleeve. This absorbent material can be soaked with any drug desired, such as an antimicrobial agent or an anesthetic agent.

The outer sleeve fits over at least that portion of the inner sleeve containing the absorbent material. The outer sleeve fits snugly over the inner sleeve to minimize evaporation of the drug from the absorbent material.

This two piece assembly maintains all of the necessary items in one unit to prepare and puncture the patient's skin. It also allows the clinician to swab a patient's skin without the need to directly contact the antimicrobial agent. The clinician merely removes the outer sleeve to expose the absorbent material on the inner sleeve and wipe the drug onto the patient's skin. Since the needle or trocar remains covered by the inner sleeve, there is no risk of an accidental stick by the needle or trocar when the drug is being applied to the patient's skin. After the patient's skin is adequately prepared, the clinician can remove the inner sleeve to expose the needle or trocar and begin the medical procedure.

BRIEF DESCRIPTION OF THE DRAWINGS

The preferred embodiments are illustrated in the drawings in which like reference numerals refer to like elements and in which.

DETAILED DESCRIPTION OF THE INVENTION

Although the needle cover assembly of this invention will be described in connection with its use to cover an introducer needle for an intravascular catheter and the needle of a hypodermic syringe, it is to be understood that the needle cover assembly of this invention can be used in conjunction with any medical device that employs a needle or trocar for puncturing a patient's skin and that requires the patient's skin to be first prepared with some drug prior to puncture.

The needle cover assembly 10 of this invention includes an inner sleeve 20 and an outer sleeve 30.

Inner sleeve 20 is formed from a hard material such as polycarbonate and includes an absorbent material 25 along a distal portion thereof. As used herein, the term distal means remote from the clinician and proximal means close to the clinician. Preferably the absorbent material 25 is cotton. However, other materials that can easily absorb liquid can be used. This allows absorbent material 25 to retain a load of drug thereon and facilitates application of the drug to the patient. For example, other materials that can be used to form absorbent material 25 include nylon, rayon, urethane or a blend of any of the previously mentioned materials.

Absorbent material 25 can be bonded to inner sleeve 20 by any standard means such as by mechanical engagement, solvent bonding, sonic welding or by use of an adhesive.

Typically, a drug in a liquid state is absorbed by absorbent material 25. The drug used can be an antimicrobial agent such as alcohol, iodine or chlorhexidine. However, other drugs, such as an anesthetic material could be used. In addition, ink could be used to allow the clinician to mark the location on the skin where the procedure is to occur.

Figure 1:
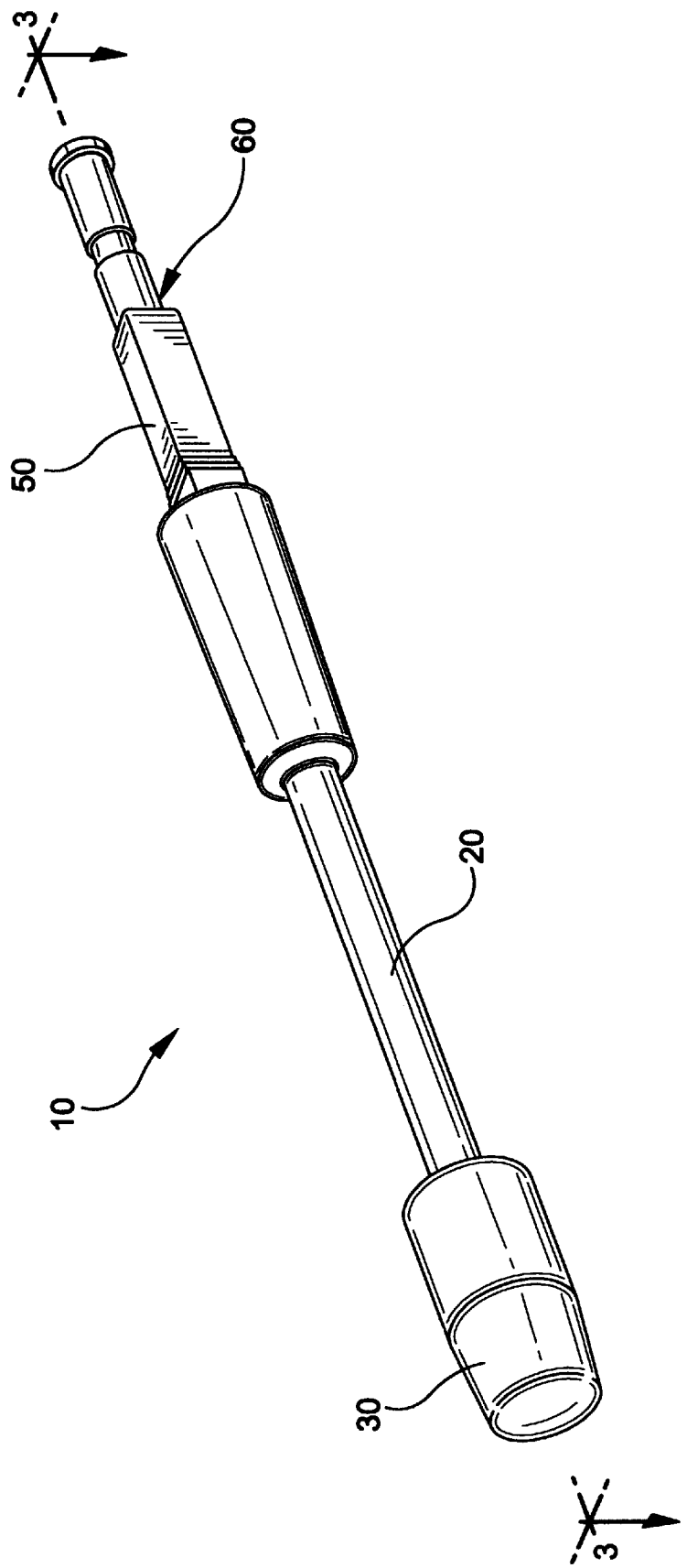
FIG. 1 is a perspective view of the needle cover assembly of this invention used in conjunction with an intravascular catheter.
Figure 2:
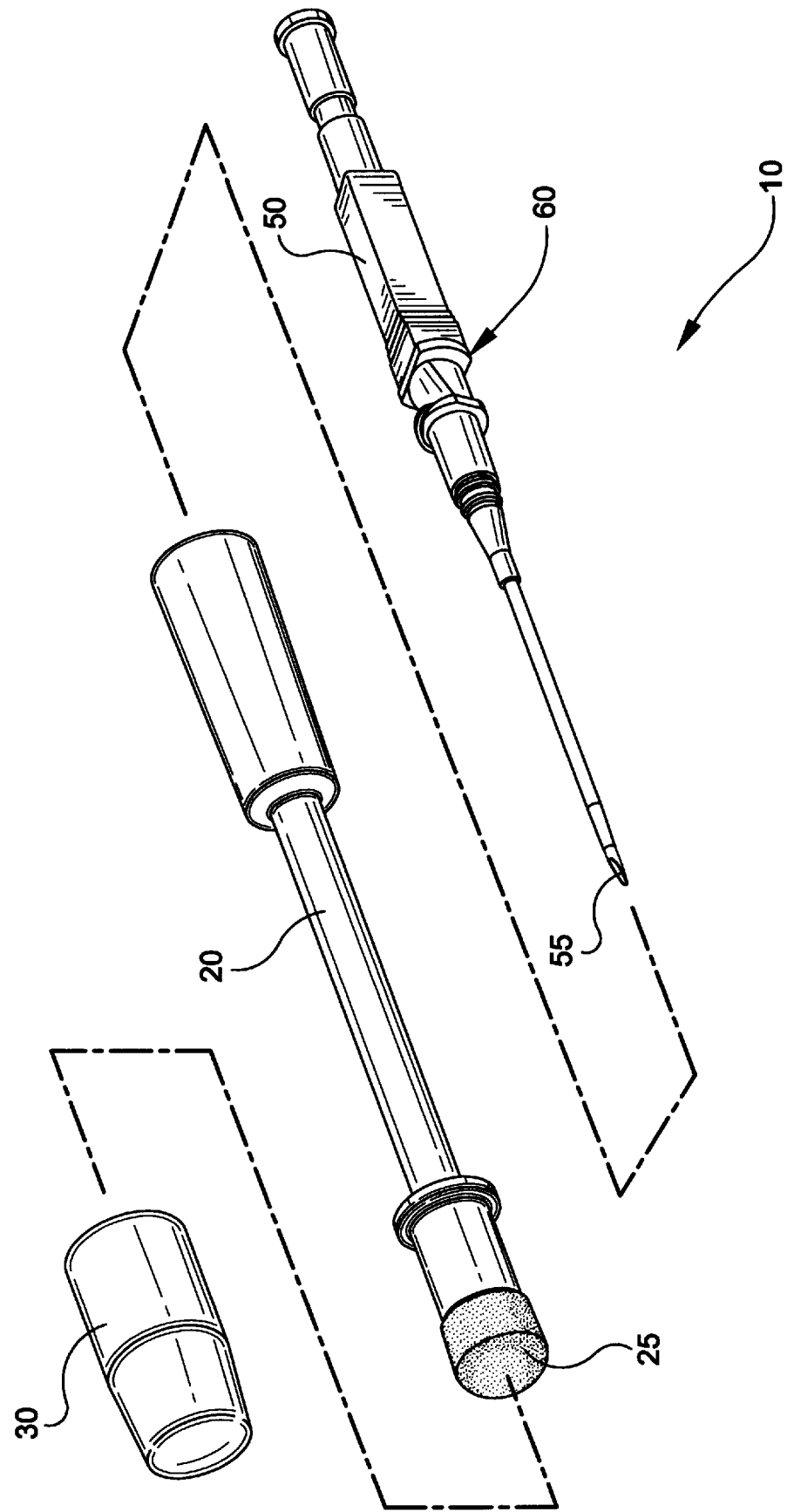
FIG. 2 is an exploded perspective view of the needle cover assembly of this invention used in conjunction with an intravascular catheter.
Figure 3:
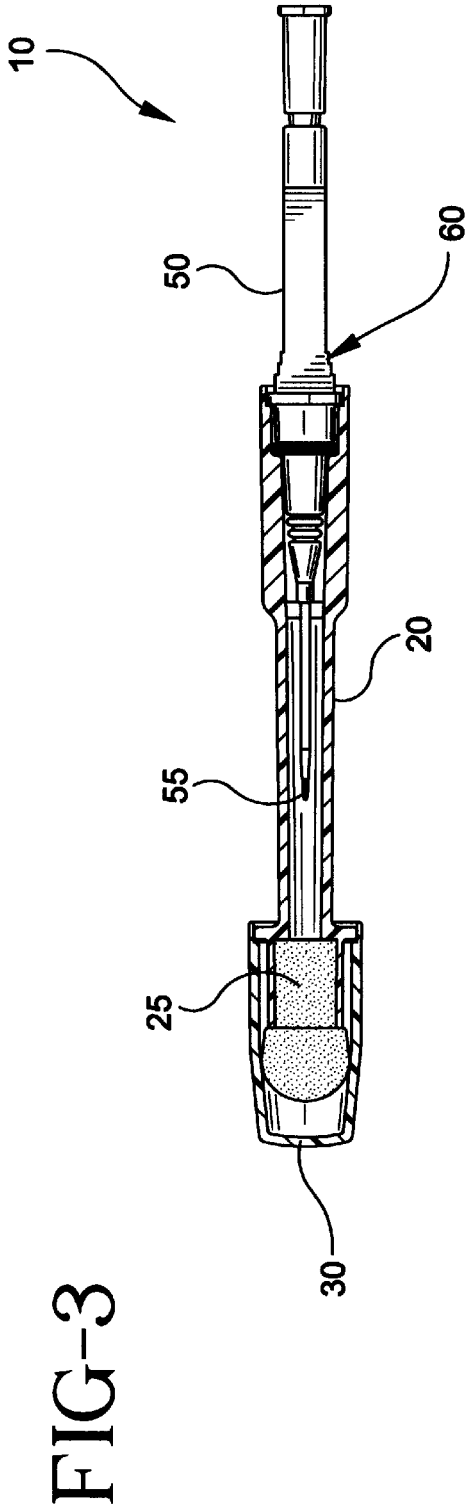
FIG. 3 is a side elevation view partially in cross section taken along line 3—3 in FIG. 1 of the needle cover assembly of this invention used in conjunction with an intravascular catheter.
Figure 4:
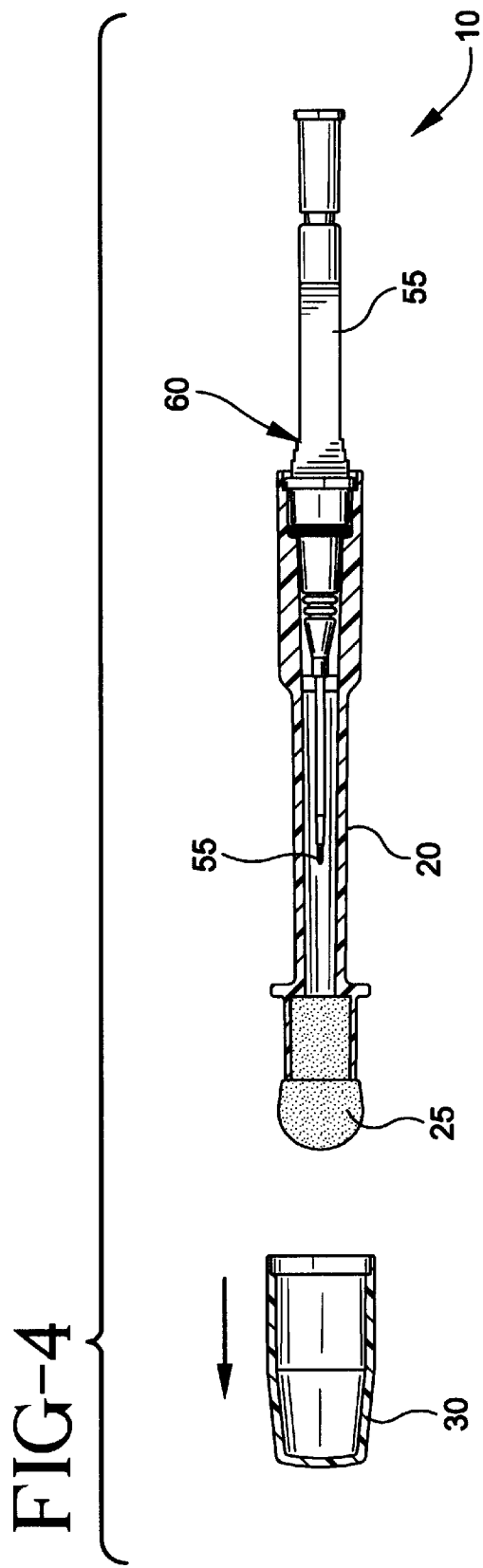
FIG. 4 is a view similar to that shown in FIG. 3 but with the outer sleeve removed.
Figure 5:
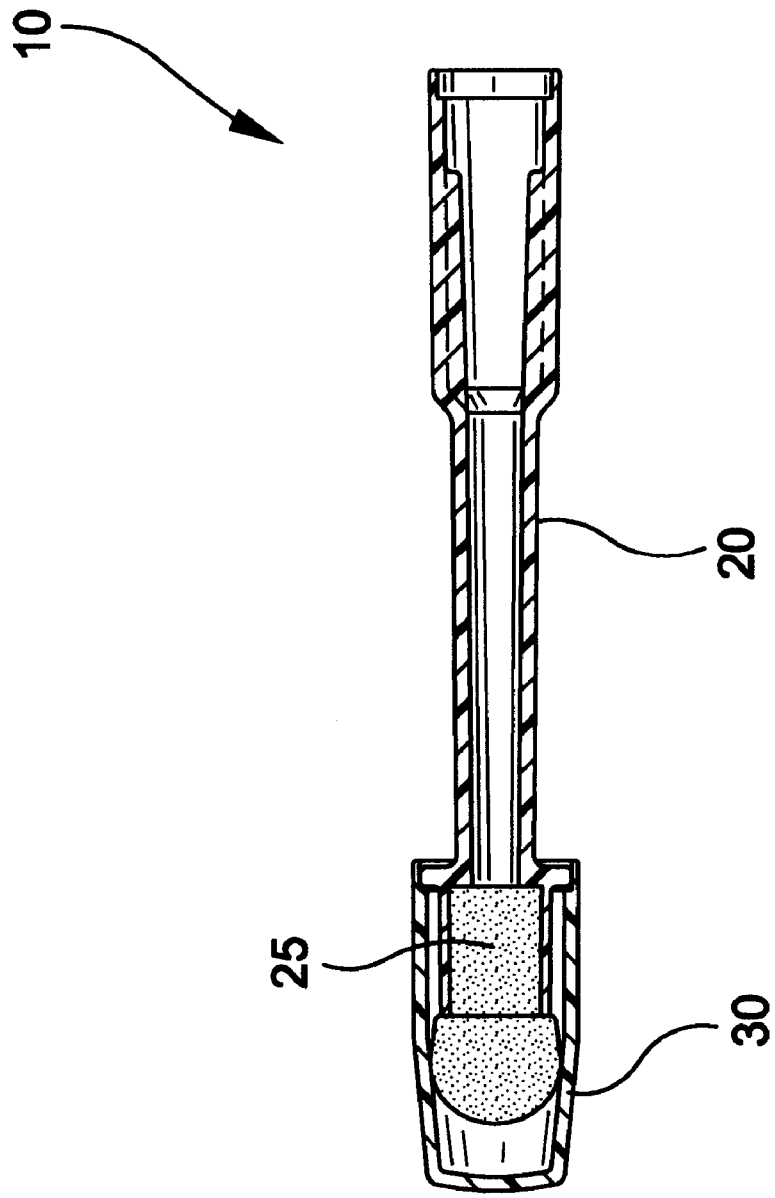
FIG. 5 is a cross sectional view of the needle cover of this invention.

The proximal end of inner sleeve 20 fits snugly on the needle hub 50 of the medical device 60 employing the needle 55 connected to needle hub 50. In the embodiment shown in FIG. 2 the medical device 60 is a catheter adapter and has a cannula 65 that extends outwardly from needle hub 50 surrounding the needle 55. The distal end of the needle 55 extends outwardly slightly from the cannula to allow the medical device 60 to penetrate the skin of a patient. Inner sleeve 20 has a longitudinal dimension that allows it to extend along needle 55 to completely encase needle 55 and prevent premature exposure of needle 55.

Outer sleeve 30 can be formed from a hard and rigid material such as polycarbonate. However, other materials such as foil or polyethylene could be used. All that is required is that the material used to form outer sleeve 30 have a low moisture transmission rate. Outer sleeve 30 fits snugly over at least that portion of inner sleeve 20 carrying absorbent material 25. The engagement between outer sleeve 30 and inner sleeve 20 should be airtight to minimize evaporation of the drug from absorbent material 25 and to maintain a sterile barrier. The evaporation rate will depend in large measure on the volatility of the drug used with absorbent material 25 as well as the moisture transmission rate of the material used to form outer sleeve 30.

When needle cover assembly 10 is used in conjunction with medical device 60, the combination of inner sleeve 20 and outer sleeve 30 serve to cover needle 55 and prevent premature exposure of needle 55 prior to the time when the medical procedure is to occur. Outer sleeve 30 also serves to cover absorbent material 25 to prevent evaporation of the drug included on absorbent material 25 prior to use and to prevent unwanted application of the drug from absorbent material 25 to some surface.

When it is desired to prepare a patient's skin prior to puncture, outer sleeve 30 is removed from inner sleeve 20. This exposes absorbent material 25 and allows the clinician to swab the patient's skin with absorbent material 25 and transfer the drug from absorbent material 25 to the patient's skin. This is done by having the clinician hold inner sleeve 20 during the swabbing step. Since inner sleeve 20 is formed from a hard and rigid material and completely covers needle 55, there is very little risk that the patient will be accidentally stabbed by needle 55 during the swabbing step.

After the patient's skin has been thoroughly swabbed with absorbent material 25, inner sleeve 20 can be removed from needle 55. Thereafter, the patient's skin can be punctured by needle 55.

Thus, it is seen that a needle cover assembly is provided that minimizes the number of separate items needed to prepare a patient's skin and cover a needle or trocar of a medical device and that allows a clinician to disinfect a patient's skin without the need for the clinician to directly contact the antimicrobial agent.

I claim:

1. A needle cover assembly comprising:

a needle having a sharp distal end and a proximal end;

an inner sleeve removably fitted over said needle to encase said needle in a protective environment within said inner sleeve, said inner sleeve having an external surface;

an absorbent material affixed to the external surface of said inner sleeve;

an outer sleeve engaged to the external surface of said inner sleeve so as to provide a relatively sealed chamber between said inner sleeve and said outer sleeve enclosing said absorbent material, said outer sleeve being removable from said inner sleeve to expose said absorbent material while retaining said needle encased within said inner sleeve; and a catheter adapter having a cannula extending therefrom and positioned about said needle.

2. A needle cover assembly as defined in claim 1 wherein said needle comprises a needle hub at said proximal end and said inner sleeve is removably connected to said needle hub.

* * * * *